United States Patent
Scott

(10) Patent No.: US 11,147,986 B2
(45) Date of Patent: Oct. 19, 2021

(54) TEMPORALLY FEATHERED RADIATION THERAPY

(71) Applicant: THE CLEVELAND CLINIC FOUNDATION, Cleveland, OH (US)

(72) Inventor: Jacob Scott, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

(21) Appl. No.: 16/636,112

(22) PCT Filed: Aug. 6, 2018

(86) PCT No.: PCT/US2018/045348
§ 371 (c)(1),
(2) Date: Feb. 3, 2020

(87) PCT Pub. No.: WO2019/028453
PCT Pub. Date: Feb. 7, 2019

(65) Prior Publication Data
US 2020/0179720 A1 Jun. 11, 2020

Related U.S. Application Data

(60) Provisional application No. 62/541,181, filed on Aug. 4, 2017.

(51) Int. Cl.
*A61N 5/10* (2006.01)
(52) U.S. Cl.
CPC .......... *A61N 5/1031* (2013.01); *A61N 5/1039* (2013.01)
(58) Field of Classification Search
CPC .... A61N 5/103; A61N 5/1031; A61N 5/1039; A61N 5/1042
See application file for complete search history.

(56) References Cited

U.S. PATENT DOCUMENTS 6,142,925 A * 11/2000 Siochi .................... A61N 5/103
600/1
6,477,229 B1 * 11/2002 Grosser ............... A61N 5/1031
378/65

(Continued)

FOREIGN PATENT DOCUMENTS

DE      10122903 A1   4/2012
GB      2545018 A    6/2017

OTHER PUBLICATIONS

Thames Jr, Howard D., et al. "Changes in early and late radiation responses with altered dose fractionation: implications for dose-survival relationships." International Journal of Radiation Oncology* Biology* Physics 8.2 (1982): 219-226.

(Continued)

*Primary Examiner* — Dani Fox
*Assistant Examiner* — Soorena Kefayati
(74) *Attorney, Agent, or Firm* — Tarolli, Sundheim, Covell & Tummino LLP

(57) ABSTRACT

The effects of acute toxicity from a radiation procedure can be reduced without altering the radiation dose by temporally feathering the radiation procedure. Using temporal feathering, the radiation procedure delivers a total amount of radiation that is weighted amounts of radiation per day. The weighted amounts of radiation can be delivered according to a sequence plan that ensures the total dose of radiation is administered in the time period. The sequence plan includes one day of a high fractional dose of radiation and four days of a low fractional dose of radiation.

18 Claims, 9 Drawing Sheets

(56) References Cited

U.S. PATENT DOCUMENTS

| | | | | |
|---|---|---|---|---|
| 9,764,162 | B1* | 9/2017 | Willcut | A61B 6/5294 |
| 9,956,428 | B2* | 5/2018 | Kelly | A61N 5/103 |
| 2004/0165696 | A1* | 8/2004 | Lee | G16H 30/20 378/65 |
| 2009/0110145 | A1* | 4/2009 | Lu | A61N 5/103 378/65 |
| 2012/0123184 | A1* | 5/2012 | Otto | A61N 5/1067 600/1 |
| 2012/0136194 | A1* | 5/2012 | Zhang | A61N 5/103 600/1 |
| 2012/0136677 | A1* | 5/2012 | Ziegenhein | G16H 20/40 705/2 |
| 2013/0077752 | A1* | 3/2013 | Zankowski | A61N 5/1039 378/65 |
| 2013/0150646 | A1* | 6/2013 | Scholz | A61N 5/1031 600/1 |
| 2013/0204121 | A1* | 8/2013 | Andresen | A61B 6/032 600/411 |
| 2013/0217948 | A1* | 8/2013 | Mihaylov | A61N 5/1031 600/1 |
| 2014/0105355 | A1* | 4/2014 | Toimela | A61N 5/1031 378/41 |
| 2016/0023018 | A1* | 1/2016 | Zhang | A61B 5/08 600/1 |
| 2016/0051841 | A1* | 2/2016 | Nguyen | A61N 5/1064 600/1 |
| 2016/0129282 | A1* | 5/2016 | Yin | G16H 20/40 600/1 |
| 2016/0140300 | A1* | 5/2016 | Purdie | A61N 5/103 705/2 |
| 2016/0213947 | A1* | 7/2016 | Han | A61N 5/1037 |
| 2017/0083682 | A1* | 3/2017 | McNutt | A61N 5/103 |
| 2017/0186153 | A1* | 6/2017 | Enderling | A61N 5/1039 |
| 2017/0259083 | A1* | 9/2017 | Nakatsugawa | A61N 5/1049 |
| 2020/0038683 | A1* | 2/2020 | Schadewaldt | A61N 5/1038 |
| 2020/0246635 | A1* | 8/2020 | Sjolund | A61N 5/1038 |
| 2020/0289848 | A1* | 9/2020 | Perko | A61N 5/1031 |

OTHER PUBLICATIONS

Atun, Rifat, et al. "Expanding global access to radiotherapy." The lancet oncology 16.10 (2015): 1153-1186.

Scott, Jacob G., et al. "A genome-based model for adjusting radiotherapy dose (GARD): a retrospective, cohort-based study." The Lancet Oncology 18.2 (2017): 202-211.

Hall, Eric J., and Amato J. Giaccia. Radiobiology for the Radiologist. vol. 6. 2006.

Dirix, Piet, and Sandra Nuyts. "Evidence-based organ-sparing radiotherapy in head and neck cancer." The lancet oncology 11.1 (2010): 85-91.

Emami, Bahman, et al. "Tolerance of normal tissue to therapeutic irradiation." International Journal of Radiation Oncology* Biology* Physics 21.1 (1991): 109-122.

Fowler, John F. "The linear-quadratic formula and progress in fractionated radiotherapy." The British journal of radiology 62.740 (1989): 679-694.

Jones, Bryan, et al. "The role of biologically effective dose (BED) in clinical oncology." Clinical oncology 13.2 (2001): 71-81.

Fowler, Jack F., James S. Welsh, and Steven P. Howard. "Loss of biological effect in prolonged fraction delivery." International Journal of Radiation Oncology* Biology* Physics 59.1 (2004): 242-249.

Rockne, Rockhill, et al. "Predicting the efficacy of radiotherapy in individual glioblastoma patients in vivo: a mathematical modeling approach." Physics in Medicine & Biology 55.12 (2010): 3271.

Stocks, Theresa, et al. "A stochastic model for the normal tissue complication probability (NTCP) and applications." Mathematical medicine and biology: a journal of the IMA 34.4 (2017): 469-492.

PCT International Search Report and Written Opinion for corresponding International Application Serial No. PCT/US2018/045348, dated Nov. 19, 2018, pp. 1-16.

* cited by examiner

TEMPORALLY FEATHERED RADIATION THERAPY

RELATED APPLICATIONS

This application claims the benefit of U.S. Provisional Application No. 62/541,181, filed Aug. 4, 2017, entitled "TEMPORAL FEATHERING AS A METHOD OF NORMAL TISSUE TOXICITY REDUCTION IN INTENSITY MODULATED RADIATION THERAPY." This provisional application is hereby incorporated by reference in its entirety for all purposes.

TECHNICAL FIELD

The present disclosure relates generally to radiation therapy and, more specifically, to systems and methods for temporally feathering a radiation therapy procedure to reduce the effects of acute toxicity without altering the radiation dose.

BACKGROUND

Radiation therapy is a modality for cancer treatment involving application of ionizing radiation to the tumor. The safe and effective application of radiotherapy aims to treat the patient's tumor tissue, while sparing the patient's healthy tissue from acute toxicity. The development of intensity-modulated radiation therapy has made strides in sparing the patient's healthy tissue from acute toxicity. However, even with intensity-modulated radiation therapy, the healthy tissue of many patients still suffers from acute toxicity. While the healthy tissue has the ability to recover from acute toxicity, this recovery can take time.

Intensity-modulated radiation therapy delivers constant radiation doses at a constant time interval. The constant time interval often does not provide time for the healthy tissue to recover from acute toxicity. Such a lack of recovery can lead to a decreased quality of life for the patient, and may even lead to treatment breaks that may compromise tumor control.

SUMMARY

The present disclosure relates generally to radiation therapy and, more specifically, to systems and methods for temporally feathering a radiation therapy procedure to reduce the effects of acute toxicity without altering the radiation dose. Using temporally feathered radiation therapy, a certain radiation dose can be delivered while providing adequate time for the patient's tissue to recover from acute toxicity.

In one aspect, the present disclosure can include a system that temporally feathers a radiation therapy procedure to reduce the effects of acute toxicity without altering the radiation dose. The system includes a non-transitory memory storing instructions; and a processor configured to execute the instructions. A target volume for a radiation procedure can be determined based on at least one image. The radiation procedure includes a total dose of radiation to be administered in a time period. An organ outside of the target volume at risk of acute toxicity from the radiation procedure can be determined based on the at least one image. A sequence plan that ensures the total dose of radiation is administered in the time period can be calculated. The sequence plan includes one day of a high fractional dose of radiation and four days of a low fractional dose of radiation.

In another aspect, the present disclosure can include a method for temporally feathering a radiation therapy procedure to reduce the effects of acute toxicity without altering the radiation dose. At least a portion of the method can be performed by a system comprising a processor. The method includes receiving a radiation procedure comprising a total dose of radiation to be administered in a time period; determining a target volume for the radiation procedure based on at least one image; determining an organ outside of the target volume at risk of acute toxicity from the radiation procedure based on the at least one image; and constructing a sequence plan that ensures the total dose of radiation is administered in the time period. The sequence plan includes one day of a high fractional dose of radiation and four days of a low fractional dose of radiation.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
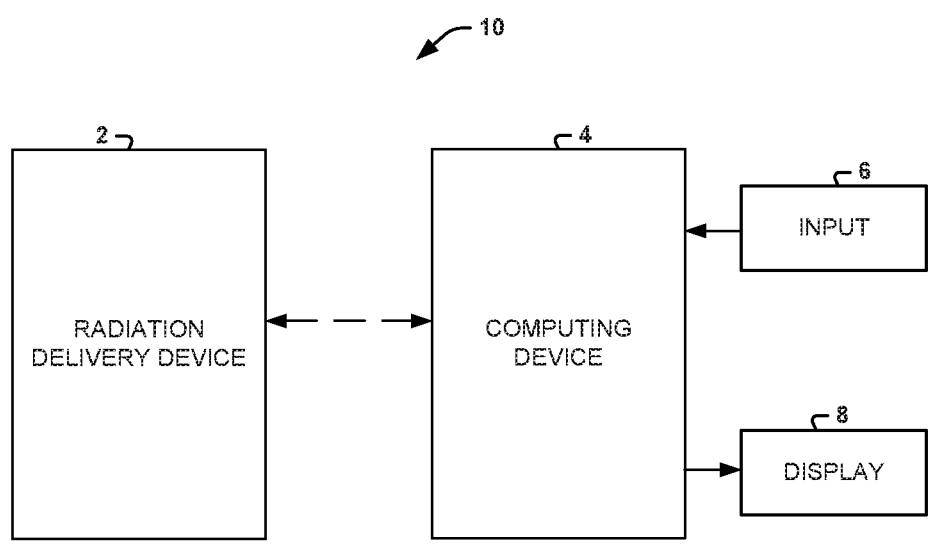
FIG. 1 is a block diagram illustration showing an example of a system that temporally feathers a radiation therapy procedure to reduce the effects of acute toxicity without altering the radiation dose in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "radiation therapy" can refer to a type of cancer treatment that uses beams of intense energy (e.g., X-rays, photons, and the like) to kill cancer cells by damaging the genetic material that controls how cancer cells grow and divide.

As used herein, the term "radiation procedure" can refer to the individualized process utilized to apply radiation therapy to a patient. A certain dose of radiation can be administered to a target volume in the patient for a certain time period. In addition to the target volume, one or more organs at risk may receive at least a portion of the dose of radiation during the radiation procedure.

As used herein, the term "target volume" can refer to a three-dimensional portion of tissue to be treated during a radiation procedure. The target volume can include a tumor and may include additional tissue located near the tumor.

As used herein, the term "organ at risk" can refer to one or more organs or tissues that may be damaged during exposure to radiation during a radiation procedure.

As used herein, the term "dose" can refer to an amount of radiation to be administered the target volume during a radiation procedure given in units of Gray (Gy). One Gy is defined as the absorption of one Joule of radiation energy per kilogram of matter. Radiation dose can vary depending on the type and stage of cancer being treated and the location of the cancer in the patient.

As used herein, the term "acute toxicity" can refer to adverse effects of radiation exposure experienced by tissues and organs outside of the target volume.

As used herein, the term "fractional dose" can refer to a portion of a prescribed radiation therapy dose that is administered to a patient at intervals within a given time period. The sum of the fractional doses within the given time period make up the prescribed radiation therapy dose.

As used herein, the term "sequence plan" can refer to a plan to administer fractional doses over a given time period. Within the sequence plan, a sum of the fractional doses over the given time period must equal the prescribed radiation therapy dose.

As used herein, the term "intensity-modulated radiation therapy (IMRT)" refers to a radiation procedure that involves an even split of a prescribed radiation therapy into equal fractional doses within a given time period.

As used herein, the term "temporal feathering" can refer to a radiation procedure that involves a split of a prescribed radiation therapy into unequal fractional doses within a given time period. Temporal feathering can include applying at least one relatively high fractional dose compared to a standard fractional dose and then delivering a plurality of relatively lower fractional dose compared to the standard fractional dose. The lower fractional doses offset the greater radiation-induced damage of the least one higher fractional dose.

As used herein, the term "image" can refer to a visual representation of the interior a patient's body for clinical analysis and medical intervention. Images used in the medical field can include X-rays, CT scans, PET Scans, ultrasounds, and MRIs.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to radiation therapy. Strides have been made to spare a patient's healthy tissue from acute toxicity while the patient undergoes radiation therapy to cure cancer. Intensity-modulated radiation therapy delivery constant radiation doses at a constant time interval. With intensity-modulated radiation therapy, however, the healthy tissue of many patients still suffers from acute toxicity because adequate time is not permitted for complete recovery from acute toxicity. Such a lack of recovery can lead to a decreased quality of life for the patient, and may even lead to treatment breaks that may compromise tumor control The present disclosure aims to provide this time for recovery while not impairing the radiation therapy according to the prescribed dose. This is accomplished by optimizing the temporal dimension through which the radiation therapy is delivered to the patient and increasing the time for recovery from acute toxicity through a treatment planning strategy called temporal feathering. Accordingly, the present disclosure relates, more specifically, to systems and methods for temporally feathering a radiation therapy procedure to reduce the effects of acute toxicity without altering the radiation dose. Using temporal feathering, the present disclosure creates an interfractional interval that facilitates recovery of the radiation-induced damage in healthy tissue, while still providing the prescribed dose of radiation therapy.

III. Systems

One aspect of the present disclosure can include a system 10 (FIG. 1) that temporally feathers a radiation therapy procedure to reduce the effects of acute toxicity without altering the radiation dose. Temporal feathering the radiation therapy procedure, at its core, alters the time frame of the radiation therapy procedure to give an organ at risk time to recover from the radiation (e.g., when radiation is delivered by a multi-dimensional distribution of radiation sources, the time averaging between the different radiation sources can be changed to ensure that the prescribed radiation dose is delivered, but to limit the exposure of the organ at risk so that the organ at risk has time to recover from acute toxicity). As such, the acute toxicity does not build up in the organ at risk, which can potentially lead to a decreased quality of life and even treatment breaks that may compromise tumor control.

The system 10 can include a radiation delivery device 2 and a computing device 4. The computing device 4 can configure the radiation procedure with the temporal feathering. The radiation delivery device 2 can deliver the radiation according to the radiation procedure with the temporal feathering. The radiation delivery device 2 can communicate with the computing device 4 in at least one direction (computing device 4 to radiation delivery device 2) according to a wired and/or wireless connection. In this case, the radiation delivery device 2 can receive the configured radiation procedure from the computing device 4. In some instances, the communication can be in two directions, allowing feedback from the radiation delivery device 2 to the computing device 4. In response to the feedback, the computing device 4 may update the radiation procedure.

The computing device 4 can have peripheral devices, including (but not limited to) an input 6 and a display 8. The input 6 can allow a user or other entity (like the radiation delivery device 2) to deliver information to the computing device 4. The display 8 can be used to provide perceivable information regarding the radiation procedure. The perceivable information can be a graphical display of a sequence plan for the radiation procedure. The perceivable information can also be a graphical display of an image to create the sequence plan. However, the perceivable information can be anything related to the radiation procedure displayed in audible or visual form.

A patient diagnosed with cancer can be prescribed a total dose of radiation to be administered to the tumor over a time period. The computing device 4 can determine the proper sequence plan for administration of the total dose over the time period. The computing device 4 aims to deliver the total dose to the tumor over the time period with a minimal risk of acute toxicity to organs at risk. The computing device 4 performs this risk management analysis using the configuration of the computing device 4 shown in FIG. 2.

Figure 2:
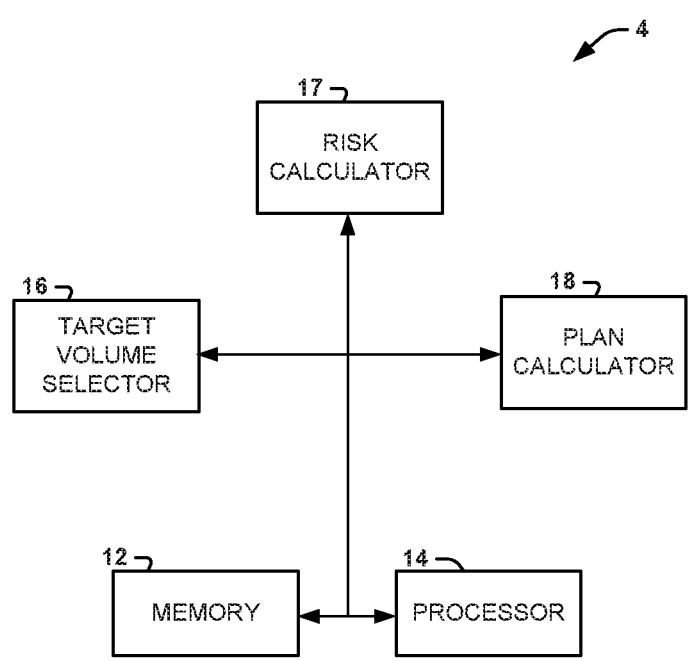
FIG. 2 is a block diagram illustration showing an example of the computing device of FIG. 1 in greater detail.

The computing device 4 can receive (via the input 6) a radiation procedure that includes a total dose of radiation to be administered to a patient in a time period. The total dose can be selected from previously used total doses (for the patient and/or other patients) based on a type of cancer, a size of cancer, a stage of cancer. As shown in FIG. 2, the computing device 4 can construct a sequence plan for the total dose during the time period. The computing device 4 includes a non-transitory memory 12 storing instructions and a processor 14 to access the memory and execute the instructions. The instructions include a target volume selector 16, a risk calculator 17, and a plan calculator 18.

The target volume selector 16 can determine the target volume for the radiation procedure based on at least one image of the patient (which can be stored in the non-transitory memory 12 and/or received from another location). The image of the patient can include at least a portion of an area that includes malignant cells. Several images can be sewn together to show the entire area of malignant cells if need be, The radiation procedure includes The image and the target volume can also be used by the risk calculator 17 to determine one or more organs outside the target volume at risk of acute toxicity from the radiation procedure. The information about the target volume and the one or more organs at risk can be used by the plan calculator 18 in constructing the sequence plan that ensures the total dose of radiation is administered in the time period, while delivering as little damaging radiation to the organ at risk as possible to reduce the effects of acute toxicity. The sequence plan developed by the plan calculator can include one day of a high fractional dose of radiation and the other days including a low fractional dose of radiation. The total dose can equal a sum of the high dose plus the number of low doses. This ensures that the total dose is delivered, but gives the organ at risk sufficient time to recover from acute toxicity due to the high dose before a high dose is delivered again.

The computing device 4 sends the sequence plan to a computer associated with the radiation delivery device 2. The computer associated with the radiation delivery device can be the computing device 4, but may be an additional computing device. The radiation delivery device 2 delivers the total dose of radiation to the patient according to the sequence plan for the time period. The computer associated with the radiation delivery device 2 can transmit information associated with the sequence plan back to the computing device 4. The computing device 4 can determine a new sequence plan for the next time period taking into account the information from the radiation delivery device.

IV. Methods

Figure 3:
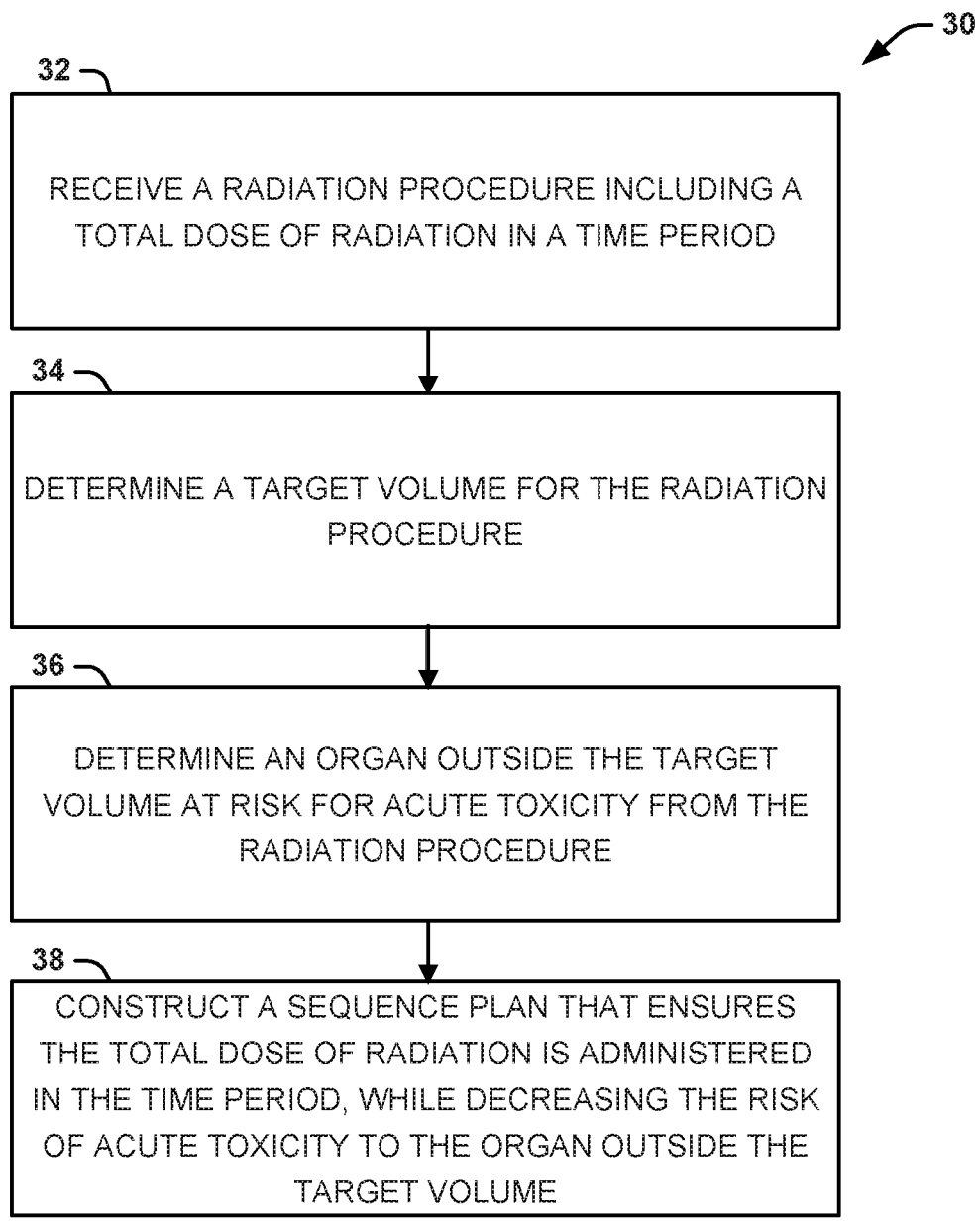
FIG. 3 is a process flow diagram of an example method for temporally feathering a radiation therapy procedure to reduce the effects of acute toxicity without altering the radiation dose in accordance with another aspect of the present disclosure.
Figure 4:
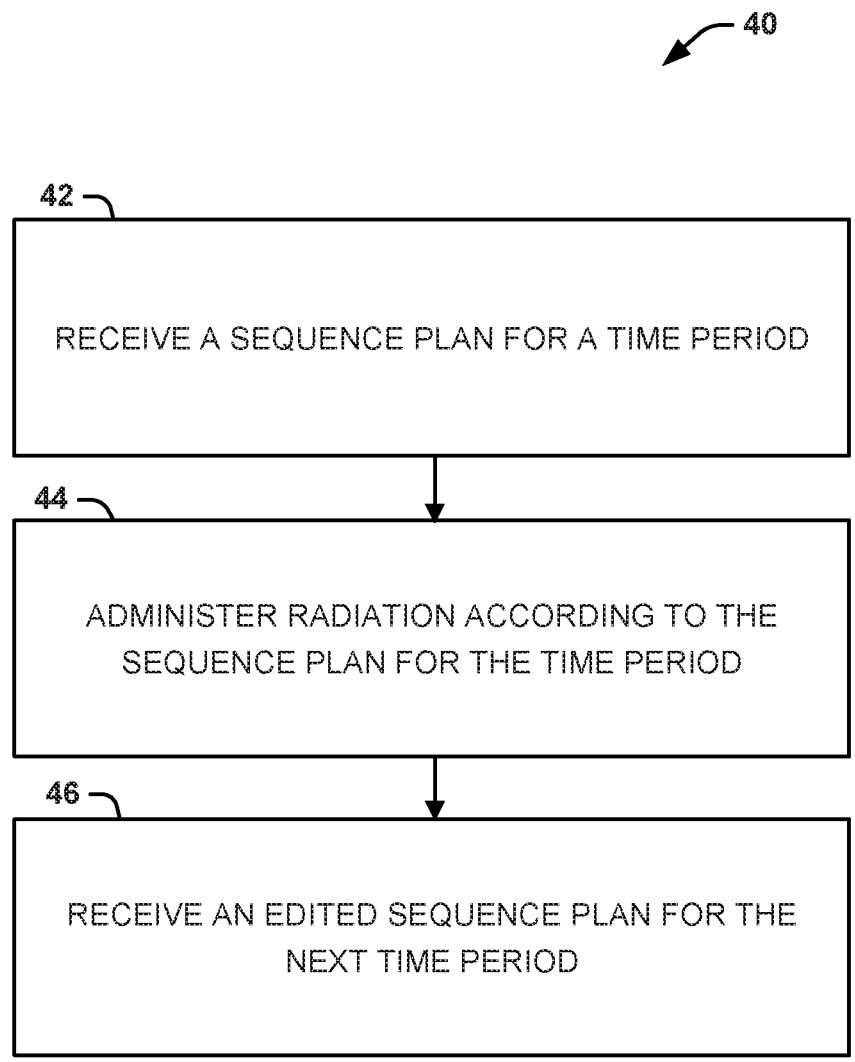
FIGS. 4-5 are process flow diagrams of additional example methods for delivering a temporally feathered sequence according to the method of FIG. 3.
Figure 5:
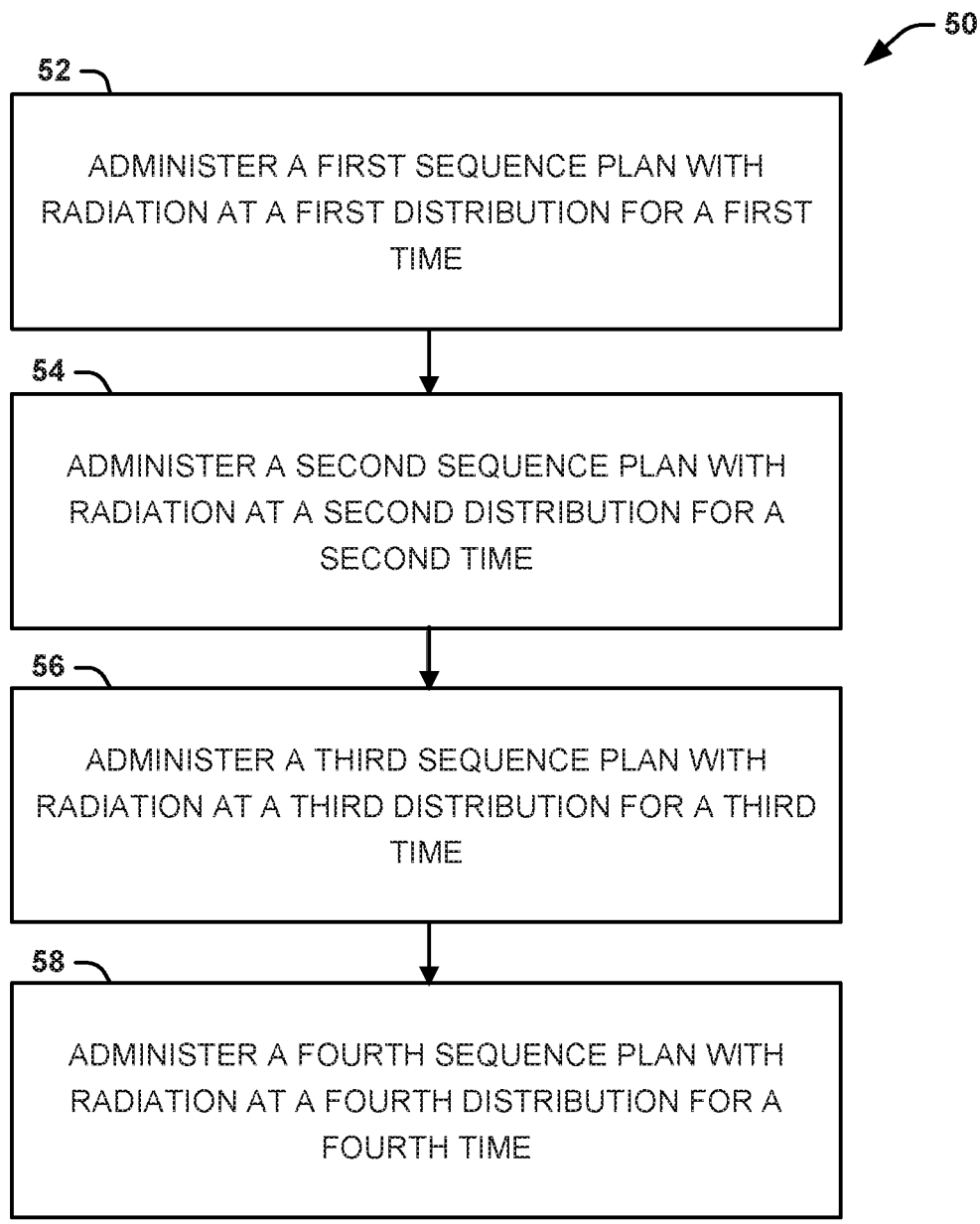

As shown in FIG. 3, another aspect of the present disclosure can include a method 30 for temporally feathering a radiation therapy procedure to reduce the effects of acute toxicity without altering the radiation dose. FIGS. 4 and 5 show additional example methods 40, 50 for delivering a temporally feathered sequence according to the method 30 of FIG. 3. The methods 30-50 can be performed at least in part by the system 10 shown in FIGS. 1 and 2.

The methods 30-50 are illustrated as process flow diagrams with flowchart illustrations. For purposes of simplicity, the methods 30-50 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30-50. The methods 30-50 can be executed by hardware—for example, at least a portion of the system 10 shown in FIGS. 1-2. One or more hardware elements of the system 10 can execute software routines to implement at least a portion of the methods 30-50. Additionally, one or more elements of the system 10 can include a non-transitory memory storing the software routines and one or more processors to execute the software routines corresponding to the at least the portion of the methods 30-50.

Referring now to FIG. 3, illustrated is a method 30 for temporally feathering a radiation therapy procedure to reduce the effects of acute toxicity without altering the radiation dose. The method 30 can be system by a system (e.g., system 10) including a processor (e.g., processor 14).

At 32, a radiation procedure can be received. The radiation procedure can include a total dose of radiation to be delivered to a patient in a time period. For example, the time period can be a week (e.g., 5 days) and the radiation procedure can include the total dose to be delivered in the week. The total dose can be split (or fractionated) for delivery to the patient during the week.

At 34, a target volume for the radiation procedure can be determined (or confirmed). The target volume, which can include one or more malignant cells, can be determined based on at least one image. At 36, an organ outside the target volume at risk for acute toxicity from the radiation procedure can be determined. The organ at risk can also be determined based on the at least one image. It should be noted that additional organs at risk can be identified.

At 38, a sequence plan that ensures the total dose of radiation is administered in the time period, while decreasing the risk of acute toxicity to the organ outside the target volume. The sequence plan can minimize the risk of acute toxicity to the organ outside the target volume. In the sequence plan, the total dose can be fractionated according to a temporal feathering procedure. For example, during a time period of a week (5 days), the total dose (TD) can be fractionated with one day of a high fractional dose (HFD) and the other days can receive a low fractional dose (LFD) so that TD=HFD+4 LFD. In other words, the high fractional dose of radiation can be greater than ⅕ times the total dose of radiation and the low fractional dose can be less than ⅕ times the total dose of radiation. The high fractional dose of radiation and the low fractional dose of radiation can be chosen based on a recovery rate of the organ outside of the target volume from acute toxicity. With temporal feathering, the total dose can be greater than a uniform total dosage delivered to the target area according to a sequence plan associated with uniform fractional doses of radiation.

Referring now to FIG. 4, illustrated is a method 40 for administering a temporally feathered radiation procedure. The method 40 can be performed by radiation delivery device 2 of the system 10. At 42, a sequence plan for a time period can be received. At 44, radiation can be administered according to the sequence plan for the time period. At 46, an edited sequence plan can be administered for the next time period. As an example, the time period can be a week, so that the sequence plan can be followed for the week. After administration for the week, the patient's response can be studied, and a revised sequence plan can be created based on the patient's response.

Referring now to FIG. 5, illustrated is a method 50 for administering a temporally feathered radiation procedure. The method 40 can be performed by radiation delivery device 2 of the system 10. The method 40 shows one example of using temporal feathering in connection with four organs at risk. It should be noted that a greater or fewer number of organs at risk may exist and the method 40 can be changed accordingly.

At 52, a first sequence plan can be administered (by a multi-dimensional radiation delivery source) with radiation at a first distribution for a first time. At 54, a second sequence plan can be administered with radiation at a second distribution for a second time. At 56, a third sequence plan can be administered with radiation at a third distribution for a third time. At 58, a fourth sequence plan can be administered with radiation at a fourth distribution for a fourth time.

V. Experimental

The following example is for the purpose of illustration only is not intended to limit the scope of the appended claims.

Through the years, researchers in the field of radiation oncology and medical physics have been innovating new ways of widening the therapeutic window by either increasing tumor control probability (TCP) or decreasing the normal tissue complication probability (NTCP). Recent works have shown the potential of spatiotemporal fractionation schemes delivering distinct radiation dose distribution in different fractions to improve the therapeutic ratio. The goal has been to maximize the mean BED of the tumor and minimize the mean BED in normal tissue by hypofractionating parts of the tumor while delivering approximately identical doses to the surrounding normal tissue. This planning strategy has been shown to result in spatiotemporal fractionation treatments that can achieve substantial reductions in normal tissue dose. However, the effect of interfractional normal tissue recovery of radiation-induced damage has not been taken into account, which when considered could lead to further reduced treatment side effects.

This example demonstrates a treatment planning strategy referred to as temporally feathered radiation therapy that takes the effect of intrafractional normal tissue recovery of radiation-induced damage into account to optimize toxicity profiles without compromising tumor control. Using temporally feathered radiation therapy, time can be leveraged to maximize the recovery of normal tissue from acute toxicity without altering total radiation dose (allowing, nonintuitively, for more occasional sublethal damage repair and prolonged repopulation phases even in the face of higher total dose delivered at the end of treatment). The total radiation dose can be delivered as a specific repetitive sequence defined with one higher than standard fractional dose followed by a plurality of lower fractional doses for a time. The plurality of lower fractional doses creates an interval between the higher than standard fractional doses, allowing more time for recovery from acute toxicity. Increasing the time for recovery can lead to improved patient quality of life, as well as a potential for dose intensification Methods Temporally Feathered Radiation Therapy The treatment planning strategy that will be discussed is termed temporally feathered radiation therapy (TFRT). Using TFRT, the fractional radiation dose delivered to organs at risk (OARs) is altered to allow for increased normal tissue recovery form radiation-induced damage with respect to conventionally fractionated intensity-modulated radiation therapy (IMRT). A TFRT plan is generated as a composite of several iso-curative (i.e., same tumor dose) plans each with altered constraints on particular OARs of interest. In each of these TFRT plans, a single OAR would be deprioritized, allowing the optimization algorithm to reduce radiation dose and thereby toxicity to all other OARs.

In practice, a planning target volume (PTV) with five surrounding OARs of interest prescribed a standard dose of 70 Gy in 35 fractions, similar to that commonly implemented for head and neck cancers. Furthermore, consider that five treatment plans are developed, wherein each of the five OARs receives a relatively high fractional dose ($d_H$) compared to the standard fractional dose ($d_S$) once weekly, that is, 2.0 Gy. A relatively lower ($d_L$) fractional dose is then delivered the remaining 4 days of the week. With this treatment planning strategy, although greater radiation-induced damage is induced by $d_H$ once weekly, it is offset by the lower fractional dose, $d_L$, delivered over a greater amount of time—during the remaining 4 days. The composite of $d_H$ and $d_L$ is then compared to the corresponding standard fractional dose $d_S$ delivered to each OAR in a conventionally fractionated IMRT plan. In this hypothetical case, the TFRT plan is composed by 35 fractions, and each OAR of interest will receive 28 fractions of $0 < d_L < d_S$ and 7 fractions of $d_H > d_S > 0$. Fractional doses $d_L$ and $d_H$ remain unaltered during the course of treatments. For demonstrative purposes, radiotherapy treatment plans that feather five OARs are considered, though any number of OARs can be chosen for temporally feathering.

Biologically Effective Dose Model

The Linear-Quadratic (LQ) model is currently the most widely used dose-response formulation in radiotherapy. The LQ model fits to in vitro cell survival experiments and incorporates the LQ behavior of the observed cell survival curves. The linear component accounts for cell killing by DNA double strand breaks (DSBs) due to a single hit of radiation, whereas the quadratic component represents the lethal effects of two separate ionizing events that eventually cause DSBs. The surviving fraction (SF) of cells after n fractions of a radiation dose d is given by:

$$SF(d) = e^{-nd(\alpha+\beta d)} \quad \text{Equation 1}$$

where $\alpha$ (Gy$^{-1}$) and $\beta$ (Gy$^{-2}$) are tissue dependent radio-sensitivity parameters.

It follows directly from the LQ model that the biological effect (E) of n equally sized fractions of dose d is given by E=nd ($\alpha+\beta$d). This equation can be manipulated to derive biologically effective dose (BED) calculations, which is a standard quantity allowing comparison of various radiotherapy fractionation schemes. BED is dependent on inherent biologic radiosensitivity of tissues, which is termed as the $\alpha$ to $\beta$ ratio, $\alpha/\beta$. The BED is given by:

$$BED = nd\left[1 + \frac{d}{\frac{\alpha}{\beta}}\right] \quad \text{Equation 2}$$

The BED equation above applies to conventionally fractionated radiation plans in which a same fractional dose (i.e., a standard dose) is delivered daily. The BED for a standard daily treatment fraction (BED$_S$) is given by:

$$BED_S = n_S d_S\left[1 + \frac{d_S}{\frac{\alpha}{\beta}}\right] \quad \text{Equation 3}$$

where $n_S$ is the number of treatment fractions and $d_S$ is the radiation dose per fraction. The BED of temporally feathered plans BED$_{TF}$ is defined as follows:

$$BED_{TF} = n_L d_L\left[1 + \frac{d_L}{\frac{\alpha}{\beta}}\right] + n_H d_H\left[1 + \frac{d_H}{\frac{\alpha}{\beta}}\right] \quad \text{Equation 4}$$

where $n_L$ and $n_H$ refer to the number of lower dose ($d_L$) and number of higher dose ($d_H$) fractions, respectively. Lower dose fractions deliver a radiation dose less than what would be delivered in a conventionally fractionated IMRT plan, $0<d_L<d_S$. Similarly, higher dose fractions deliver a radiation dose higher than what would be delivered in a conventionally fractionated IMRT plan, $d_H>d_S>0$. Fractional doses $d_L$ and $d_H$ remain unaltered during the course of treatment and are homogeneously distributed on each OAR. The total number of fractions and their time of delivery remains the same as in conventionally fractionated IMRT and TFRT plans, that is $n_S=n_L+n_H$. Additionally, the tumor dose does not change, only the dose to OARs BED-Based Comparison of Treatment Plans The difference in the BED delivered by a conventionally fractionated IMRT plan (S) of a standard dose $d_s$ and a temporally feathered (TF) radiation therapy plan is defined as $\Delta BED=BED_S-BED_{TF}$.

Dynamical Model of Normal Tissue Complication Probability

A nonspatial dynamical model is used to simulate normal tissue response to radiation. This is a form of NTCP modeling, which is a quantitative measure of radiation-induced detriment to normal tissues. The model is formulated as a logistic differential equation that describes the recovery of normal tissues (N) from sublethal radiation-induced damage given by:

$$\frac{dN}{dt} = \mu N(t)(1-N(t)) - \delta(t_i)RT(d)N(t)(1-N(t)) \quad \text{Equation 5}$$

where the organ-specific parameter $\mu>0$ represents the recovery rate of radiation-induced damage. Before radiation, the simulated OAR is at tissue homeostasis with a 1% turnover rate, thus N(0)=0.99. Then N(t)<N(0) represents the level of normal tissue damage by radiotherapy (small values of N(t) relate to severe damage), and (N(0)−N(t)) is used as an indication of the radiation induced toxicity. The logistic differential Equation 5 used to model normal tissue recovery simulates a decay of toxicity to zero over time. This is based on clinical observations revealing that not all patients develop late toxicities, and, more importantly, that acute toxicities normally do go to zero on rather short time scales. Furthermore, this model is used to compare conventionally fractionated and temporally feathered radiotherapy plans under the same conditions, which does not influence the ability to compare planning techniques. The model was solved numerically in Matlab (www.mathworks.com).

The effect of radiation is included by the loss term $\delta(t_i)RT(d)N(t)(1-N(t))$ in Equation 5, where $\delta(t_i)$ is the Dirac delta function equal to one at the time of irradiation $t_i$ and zero otherwise. The structure of this loss term models the growing effect of radiation therapy with increasing number of treatment fractions. In fact, it is known that as treatment fractions accumulate the observed radiation-induced acute toxicities become increasingly apparent. Clinically normal tissue toxicities that increase in severity midway and toward the end of radiation therapy treatments are observed. The function $RT(d)=(1-e^{-\alpha d-\beta d^2})$ is based on the radiobiological LQ model in Equation 1. More precisely, RT(d) represents the "injured fraction" of normal cells receiving a radiation dose d, that is 1−surviving fraction of cells. Thus, for low radiation doses, the injured fraction of normal cells due to radiation must be small, thereby RT(d) must be close to zero. On the other hand, high radiation doses will result in more killed normal cells for which RT(d) tends to one. Furthermore, both the delivery of each treatment fraction and response to radiation are assumed to be instantaneous.

It should be noted that the LQ model is used to describe the immediate radiation response of normal tissue and a dynamical NTCP model to describe normal tissue repair of radiation-induced damage during fractions and over the entire treatment time.

NTCP-Based Comparison of Treatment Plans

The difference between OAR toxicity induced by a conventionally fractionated IMRT plan ($N_S(t_{end})$) and a TFRT plan ($N_{TF}(t_{end})$) at the end of treatment $t_{end}$ is denoted by $\Delta NTCP=N_S(t_{end})-N_{TF}(t_{end})$. Positive values ($\Delta NTCP>0$) favor TFRT over IMRT plans.

Overall and Maximum Potential Benefit of TFRT over Conventionally Fractionated IMRT The normal tissue toxicity reduction of TFRT over conventionally planned IMRT is estimated by using a term referred to as overall potential benefit (OPB$_{TF}$). For any given combination of the organ-specific recovery rate $\mu$ and the fractional radiation dose $d_S$ delivered by a conventionally fractionated IMRT plan, OPB$_{TF}$ is the ratio of simulated TFRT plans with $0<d_m\leq d_L\leq d_S$ and $0<d_S\leq d_H\leq d_m$ that result in $\Delta NTCP>0$ and deliver higher total doses than the corresponding IMRT plans. In this study, $d_m$ and $d_M$ are the minimum lower dose ($d_L$) and the maximum higher dose ($d_H$) considered to generate the TFRT plans.

The maximum potential benefit ($MAX_{TF}$) of TFRT over conventionally planned IMRT is defined as the maximum $\Delta NTCP>0$ of simulated TFRT plans delivering higher total doses than the corresponding IMRT plans.

Results

BED Model Simulations

The BED model is considered to compare TFRT and conventionally fractionated IMRT under varying conditions. To this end, an OAR was considered at a physiologic equilibrium and characterized by an $\alpha/\beta$ ratio of 3 Gy. Furthermore, TFRT plans were simulated with $d_m \le d_L \le d_S$ and $d_S \le d_H \le d_M$ consisting of 28 fractions ($n_L$) of $d_L < d_S$ and 7 fractions ($n_H$) of $d_H > d_S$, and the corresponding conventionally fractionated IMRT plans delivering $d_S$ in 35 fractions. For illustrative purposes, $d_m = (d_S - 0.5$ Gy$)$ and $d_M = (d_S + 2.5$ Gy$)$ with a dose increment of 0.01 Gy between $d_m$ and $d_S$, as well as between $d_S$ and $d_M$.

Figure 6:
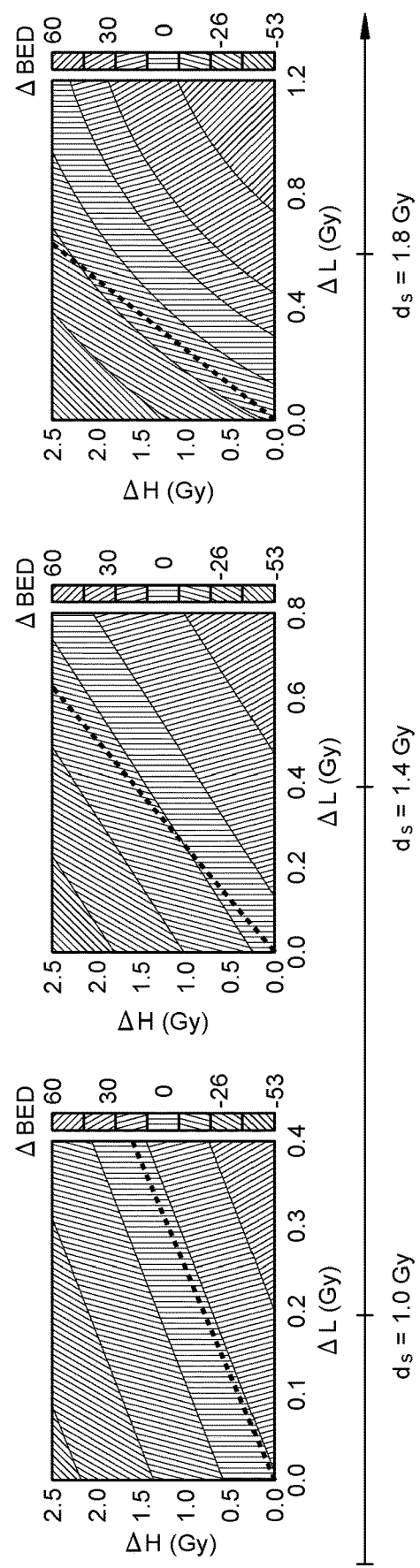
FIG. 6 shows a comparison of conventionally fractionated IMRT and TFRT based on the biology effective dose (BED) model.

FIG. 6 illustrates $\Delta BED = (BED_S - BED_{TF})$ between different TFRT and conventionally planned IMRT plans (Equations 3 and 4). Irrespective of $d_S$, TFRT plans result only in a lower BED when the total dose ($28\ d_L + 7\ d_H$) delivered to the OAR of interest is less compared to the standard IMRT plan ($35\ d_c$). Further, combinations of $d_L$ and $d_H$ exist in which $BED_{TF} > BED_S$ even when the total dose by TFRT plans is less than in the conventionally fractionated IMRT plan. These results hold irrespective of the $\alpha/\beta$ ratio of the OAR of interest. The BED formulation does not account for the effect of interfractional normal tissue recovery of radiation-induced damage, and therefore is not a suitable model to evaluate the potential benefit of TFRT. This highlights the need for models that account for the dynamic of normal tissue recovery from radiation-induced damage between treatment fractions to access the feasibility of TFRT.

Dynamical NTCP Model Simulations

Figure 7:
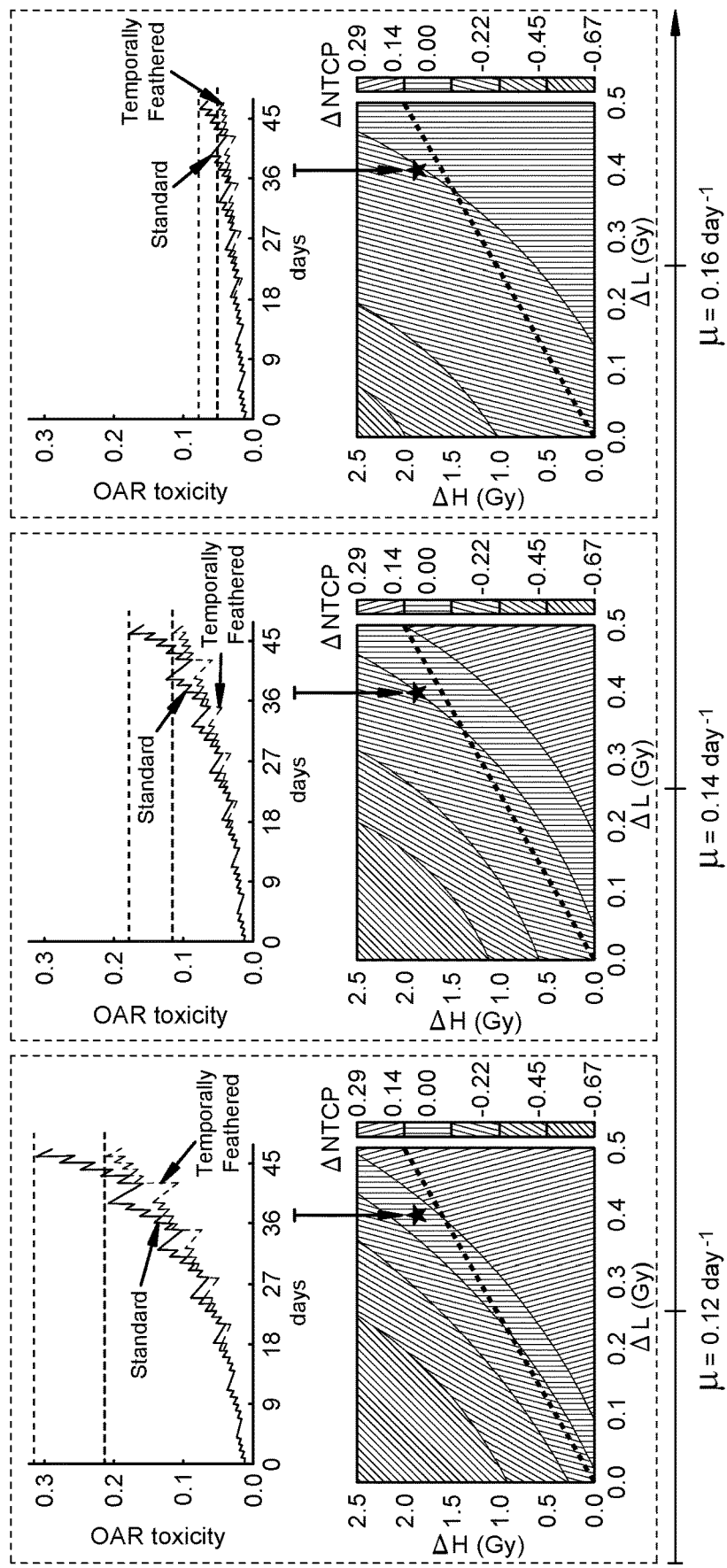
FIG. 7 shows a comparison and representation of NTCP and radiation-induced OAR toxicity between conventionally fractionated IMRT and TFRT with varying organ specific recovery rates ($\mu$)
Figure 8:
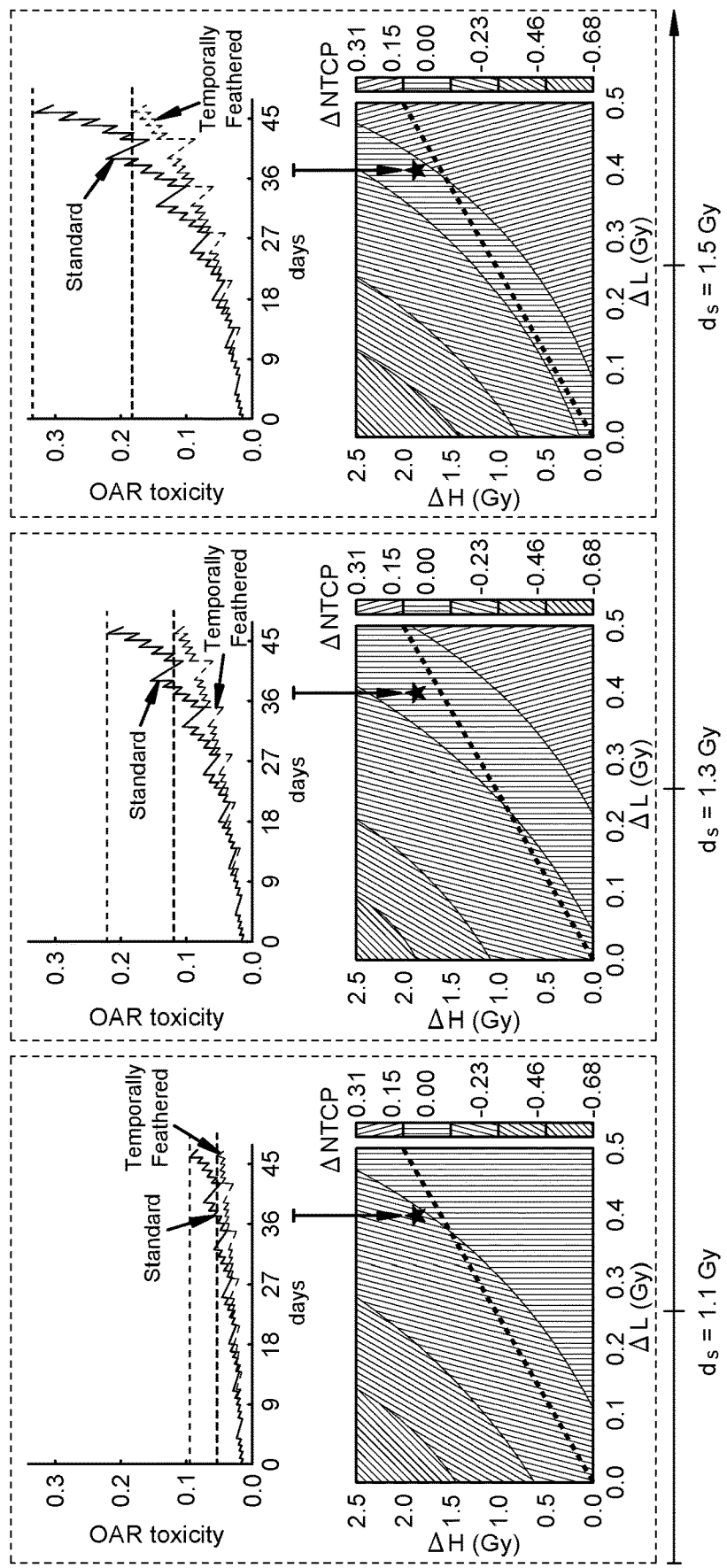
FIG. 8 shows a comparison and representation of NTCP and radiation-induced OAR toxicity between conventionally fractionated IMRT and TFRT with varying standard fractional doses ($d_s$)

The normal tissue complication probability (NTCP) of TFRT compared to conventionally fractionated IMRT is simulated by implementing the dynamical NTCP model presented in Equation 5. The conditions are the same those described as above with respect to the BED model simulations. NTCP model simulations reveal a range of treatment planning conditions in which TFRT plans reduce radiation-induced toxicity to OARs compared to conventional planned IMRT plans. These conditions are dependent on $d_L$ and $d_H$, as well as on the organ-specific recovery rates $\mu$, associated with radiation-induced damage. This is shown in FIGS. 7 and 8, which represent $\Delta NTCP$ for TFRT and conventionally fractionated IMRT plans with varying $\mu$ and $d_S$ values, respectively. As exhibited by FIGS. 7 and 8, certain combinations of $d_L$ and $d_H$ delivering higher total doses in TFRT plans as compared to conventionally fractionated IMRT plans yet reduce the overall radiation-induced OAR toxicity (shown in the bottom panels of FIGS. 7 and 8). The therapeutic gain by TFRT plans increases as treatment progresses (shown in the top panels of FIGS. 7 and 8). Furthermore, FIGS. 7 and 8 show the difference between OAR toxicity induced by conventional planned IMRT and TFRT plans at the end of treatment ($\Delta NTCP$) is greater with decreasing values of $\mu$ and increasing fractional doses $d_S$. Thus, TFRT is more beneficial for reducing radiation-induced toxicity in OARs with low recovery rates $\mu$ and receiving high standard fractional doses $d_S$ with conventional planned IMRT.

Figure 9:
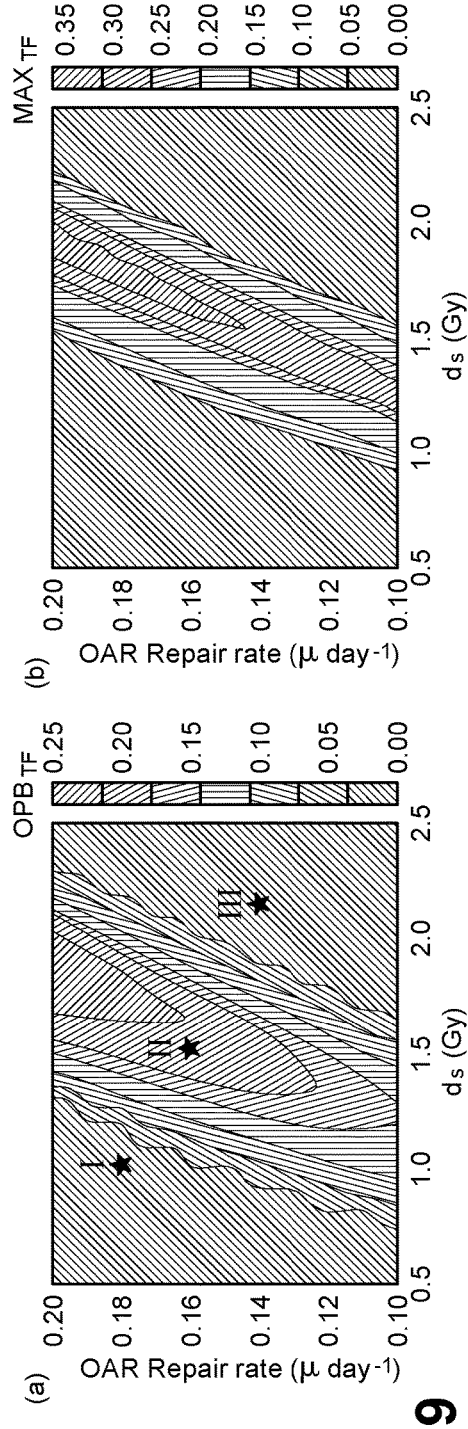
FIG. 9 shows a comparison of conventionally fractionated IMRT and TFRT with respect to the standard fractional dose ($d_s$) and organ specific recovery rate ($\mu$).
Figure 9:
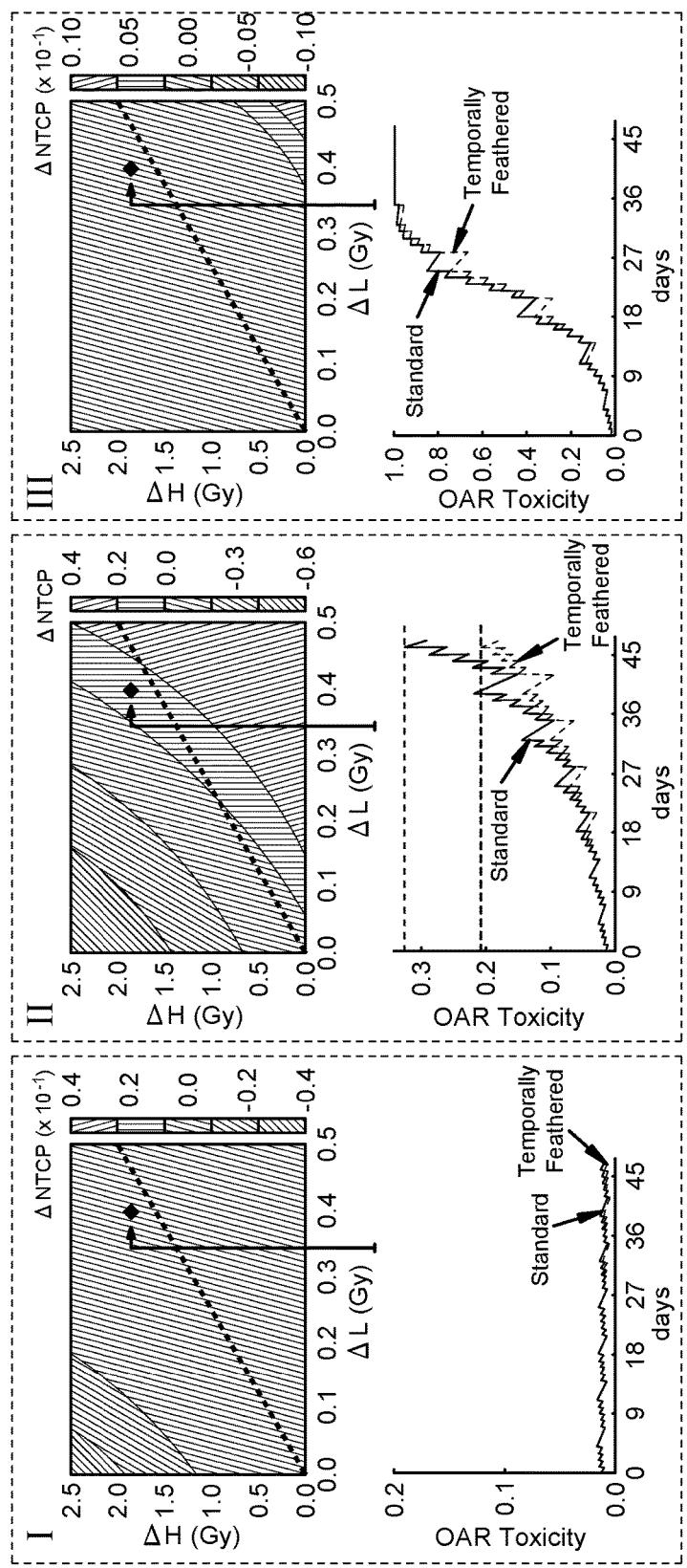

FIG. 9 summarizes the impact of organ-specific treatment parameters on the potential benefit of TFRT over conventionally fractionated IMRT. For each combination of $\mu$ and $d_S$ considered, FIGS. 9 (a) and (b) show the overall potential benefit ($OPB_{TF}$) and maximum potential benefit ($MAX_{TF}$) of TFRT plans over the corresponding IMRT plans. FIG. 9 shows that while keeping one of $d_S$ or $\mu$ constant and varying the other, the $OPB_{TF}$ and $MAX_{TF}$ of TFRT increase until a maximum level and then decrease again. This suggests that for each OAR characterized by a specific recovery rate $\mu$, TFRT plans can be designed to reduce OAR toxicity if the standard fractional dose $d_S$ delivered by a conventionally fractionated IMRT plans lies in a certain range. Furthermore, there exists an optimal dose $d_S$ in that range for which OAR toxicity reduction with TFRT is greater. Similarly, OARs receiving a specific standard fractional dose $d_S$ with conventional planned IMRT can be temporally feathered if the recovery rate $\mu$ is in a certain range. This evidences that both $d_S$ and $\mu$ must be considered together when determining the OAR toxicity reduction from TFRT over conventionally planned IMRT.

From the above description, those skilled in the art will perceive improvements, changes and modifications. Such improvements, changes and modifications are within the skill of one in the art and are intended to be covered by the appended claims.

What is claimed is:

1. A system comprising:
    a non-transitory memory storing instructions; and
    a processor configured to execute the instructions to:
        determine a target volume for a radiation procedure based on at least one image, wherein the radiation procedure comprises a total dose of radiation to be administered in a time period comprising three or more days;
        determine an organ outside of the target volume at risk of acute toxicity from the radiation procedure based on the at least one image; and
        construct a sequence plan that ensures the total dose of radiation is administered in the time period, wherein the sequence plan comprises one day of a high fractional dose of radiation and two or more days of a low fractional dose of radiation each, wherein the sum of the high fractional dose of radiation and the low fractional doses of radiation equals the total dose of radiation administered in the time period, wherein administering the low fractional doses of radiation over the two or more days allows time for the organ outside of the target volume time to recover from acute toxicity; and
        send the sequence plan to a computing device associated with a radiation delivery device, wherein, in response, the radiation device:
            delivers the total dose of radiation to a patient associated with the target volume according to the sequence plan, and
            transmits information associated with the sequence plan back to the computing device, wherein the computing device determines a new sequence plan for a next time period based on the transmitted information.

2. The system of claim 1, wherein the processor is configured to determine a second organ outside the target volume at risk of acute toxicity from the radiation procedure based on the at least one image; and
    construct a second sequence plan that ensure the total dose of radiation is administered in a second time period, wherein the second sequence plan comprises one day of a high fractional dose of radiation and four days of a low fractional dose of radiation delivered at a different distribution than the first sequence plan.

3. The system of claim 1, wherein the sequence plan is constructed to reduce the risk of acute toxicity in the organ outside of the target volume while still delivering the total dose of radiation to the target volume.

4. The system of claim 1, wherein the target volume comprises malignant cells.

5. The system of claim 1, wherein the high fractional dose of radiation is greater than ⅕ times the total dose of radiation to be administered in the time period and the low fractional dose of radiation is less than ⅕ times the total dose of radiation.

6. The system of claim 1, wherein the total dosage is greater than a uniform total dosage delivered to the target area according to a sequence plan of uniform fractional doses of radiation.

7. The system of claim 2, wherein the processor is configured to determine a third organ outside the target volume at risk of acute toxicity from the radiation procedure based on the at least one image; and
   construct a third sequence plan that ensure the total dose of radiation is administered in a third time period, wherein the third sequence plan comprises one day of a high fractional dose of radiation and four days of a low fractional dose of radiation delivered at another different distribution than the first sequence plan and the second sequence plan.

8. The system of claim 5, wherein the high fractional dose of radiation and the low fractional dose of radiation are chosen based on a recovery rate of the organ outside of the target volume from acute toxicity.

9. A method comprising:
   receiving, by a system comprising a processor, a radiation procedure comprising a total dose of radiation to be administered in a time period comprising two or more days;
   determining, by the system, a target volume for the radiation procedure based on at least one image;
   determining, by the system, an organ outside of the target volume at risk of acute toxicity from the radiation procedure based on the at least one image; and
   constructing, by the system, a sequence plan that ensures the total dose of radiation is administered in the time period, wherein the sequence plan comprises one day of a high fractional dose of radiation and two or more days of a low fractional dose of radiation each, wherein the sum of the high fractional dose of radiation and the low fractional doses of radiation equals the total dose of radiation administered in the time period, wherein administering the low fractional doses of radiation over the two or more days allows time for the organ outside of the target volume time to recover from acute toxicity; and
   sending, by the system, the sequence plan to a computing device associated with a radiation delivery device, wherein, in response, the radiation delivery device:
      delivers the total dose of radiation to a patient associated with the target volume according to the sequence plan, and
      transmits information associated with the sequence plan back to the computing device, wherein the computing device determines a new sequence plan for a next time period based on the transmitted information.

10. The method of claim 9, further comprising displaying, by the system, a graphical representation of the sequence plan on a graphical display device.

11. The method of claim 9, further comprising:
   determining, by a system, a second organ outside the target volume at risk of acute toxicity from the radiation procedure based on the at least one image; and
   constructing, by the system, a second sequence plan that ensure the total dose of radiation is administered in a second time period, wherein the second sequence plan comprises one day of a high fractional dose of radiation and four days of a low fractional dose of radiation delivered at a different distribution than the first sequence plan.

12. The method of claim 9, wherein the sequence plan is constructed to reduce the risk of acute toxicity in the organ outside of the target volume while still delivering the total dose of radiation to the target volume.

13. The method of claim 9, wherein the target volume comprises malignant cells.

14. The method of claim 9, wherein the high fractional dose of radiation is greater than ⅕ times the total dose of radiation to be administered in the time period and the low fractional dose of radiation is less than ⅕ times the total dose of radiation.

15. The method of claim 9, wherein the total dose is greater than a uniform total dosage delivered to the target area according to a sequence plan of uniform fractional doses of radiation.

16. The method of claim 10, further comprising:
   receiving, by the system, a confirmation of the sequence plan from an input device; and
   upon receiving the confirmation, saving, by the system, the sequence plan for use in the radiation procedure.

17. The method of claim 11, further comprising:
   determining, by the system, a third organ outside the target volume at risk of acute toxicity from the radiation procedure based on the at least one image; and
   constructing, by the system, a third sequence plan that ensure the total dose of radiation is administered in a third time period, wherein the third sequence plan comprises one day of a high fractional dose of radiation and four days of a low fractional dose of radiation delivered at another different distribution than the first sequence plan and the second sequence plan.

18. The method of claim 14, wherein the high fractional dose of radiation and the low fractional dose of radiation are chosen based on a recovery rate of the organ outside of the target volume from acute toxicity.

* * * * *